(12) United States Patent
Quadri

(10) Patent No.: US 8,092,520 B2
(45) Date of Patent: Jan. 10, 2012

(54) VASCULAR PROSTHESIS CONNECTING STENT

(75) Inventor: Arshad Quadri, West Hartford, CT (US)

(73) Assignee: CardiAQ Technologies, Inc., Irvine, CA (US)

( * ) Notice: Subject to any disclaimer, the term of this patent is extended or adjusted under 35 U.S.C. 154(b) by 69 days.

(21) Appl. No.: 12/084,586

(22) PCT Filed: Nov. 9, 2006

(86) PCT No.: PCT/US2006/043526
§ 371 (c)(1),
(2), (4) Date: Apr. 13, 2009

(87) PCT Pub. No.: WO2007/058857
PCT Pub. Date: May 24, 2007

(65) Prior Publication Data
US 2009/0216314 A1    Aug. 27, 2009

Related U.S. Application Data

(60) Provisional application No. 60/735,221, filed on Nov. 10, 2005.

(51) Int. Cl.
*A61F 2/24* (2006.01)
*A61F 2/82* (2006.01)
(52) U.S. Cl. ........................ 623/1.36; 623/1.26; 623/2.18
(58) Field of Classification Search .................. 623/1.15, 623/1.16, 1.36
See application file for complete search history.

(56) References Cited

U.S. PATENT DOCUMENTS

| 5,397,355 A | 3/1995 | Marin |
| 5,411,552 A | 5/1995 | Andersen et al. |
| 5,575,818 A | 11/1996 | Pinchuk |
| 5,855,601 A | 1/1999 | Bessler et al. |
| 5,879,381 A | 3/1999 | Moriuchi et al. |
| 6,015,431 A | 1/2000 | Thornton et al. |
| 6,053,940 A | 4/2000 | Wijay |

(Continued)

FOREIGN PATENT DOCUMENTS

GB    2245495    1/1992
(Continued)

OTHER PUBLICATIONS

CPO; Canadian Office Action for 2,629,534; Jul. 20, 2010.

(Continued)

*Primary Examiner* — Thomas J Sweet
*Assistant Examiner* — Megan Wolf
(74) *Attorney, Agent, or Firm* — Knobbe Martens Olson & Bear LLP

(57) ABSTRACT

An expandable vascular stent includes an m×n array of ovals formed in a cylinder, m being the number of columns of ovals in the circumferential direction and n being the number of rows of ovals in the axial direction, and a plurality of prongs extending inwardly from the outer ends of respective ovals in rows 1 and n of the m×n array, and being arranged in facing pairs extending from axially-aligned ovals. The cylinder is expandable from an initial diameter to a pre-determined final diameter, wherein an increase in the diameter of the stent results in a substantial decrease in the length of the stent. The tube and the prongs can be made of surgical stainless steel, the tube being expandable using an angioplasty balloon; or the tube and the prongs can be made of a memory metal and the tube is self-expanding.

45 Claims, 12 Drawing Sheets

U.S. PATENT DOCUMENTS

| | | | |
|---|---|---|---|
| 6,113,612 | A | 9/2000 | Swanson et al. |
| 6,159,237 | A | 12/2000 | Alt |
| 6,168,616 | B1 | 1/2001 | Brown, III |
| 6,352,543 | B1 | 3/2002 | Cole |
| 6,425,916 | B1 | 7/2002 | Garrison et al. |
| 6,458,153 | B1 | 10/2002 | Bailey et al. |
| 6,475,237 | B2 | 11/2002 | Drasler et al. |
| 6,482,228 | B1 | 11/2002 | Norred |
| 6,511,491 | B2 * | 1/2003 | Grudem et al. ............ 606/153 |
| 6,517,573 | B1 | 2/2003 | Pollock |
| 6,676,698 | B2 * | 1/2004 | McGuckin et al. ......... 623/1.24 |
| 6,767,362 | B2 | 7/2004 | Schreck |
| 6,790,230 | B2 | 9/2004 | Beyersdorf et al. |
| 6,979,350 | B2 | 12/2005 | Moll et al. |
| 7,018,401 | B1 | 3/2006 | Hyodoh et al. |
| 7,018,406 | B2 | 3/2006 | Seguin et al. |
| 7,186,265 | B2 | 3/2007 | Sharkawy et al. |
| 7,201,772 | B2 | 4/2007 | Schwammenthal et al. |
| 7,329,278 | B2 | 2/2008 | Seguin et al. |
| 7,381,219 | B2 | 6/2008 | Salahieh et al. |
| 7,429,269 | B2 | 9/2008 | Schwammenthal et al. |
| 7,442,204 | B2 | 10/2008 | Schwammenthal et al. |
| 7,445,631 | B2 | 11/2008 | Salahieh et al. |
| 7,585,321 | B2 | 9/2009 | Cribier |
| 2003/0220683 | A1 | 11/2003 | Minasian et al. |
| 2004/0039436 | A1 | 2/2004 | Spenser et al. |
| 2004/0210304 | A1 | 10/2004 | Seguin et al. |
| 2005/0096738 | A1 | 5/2005 | Cali et al. |
| 2005/0137682 | A1 | 6/2005 | Justino |
| 2005/0137690 | A1 | 6/2005 | Salahieh et al. |
| 2005/0137695 | A1 | 6/2005 | Salahieh et al. |
| 2005/0137701 | A1 | 6/2005 | Salahieh et al. |
| 2005/0154444 | A1 | 7/2005 | Quadri |
| 2005/0234546 | A1 | 10/2005 | Nugent et al. |
| 2005/0283231 | A1 | 12/2005 | Haug et al. |
| 2006/0195183 | A1 | 8/2006 | Navia et al. |
| 2006/0212110 | A1 * | 9/2006 | Osborne et al. ............ 623/1.24 |
| 2006/0265056 | A1 | 11/2006 | Nguyen et al. |
| 2007/0010876 | A1 | 1/2007 | Salahieh et al. |
| 2007/0118206 | A1 | 5/2007 | Colgan et al. |
| 2007/0162107 | A1 | 7/2007 | Salahieh et al. |
| 2007/0213813 | A1 | 9/2007 | Von Segesser et al. |
| 2007/0255391 | A1 | 11/2007 | Hojeibane et al. |
| 2008/0071363 | A1 | 3/2008 | Tuval et al. |
| 2008/0125859 | A1 | 5/2008 | Salahieh et al. |
| 2008/0133003 | A1 | 6/2008 | Seguin |
| 2008/0140189 | A1 | 6/2008 | Nguyen et al. |
| 2008/0208328 | A1 | 8/2008 | Antocci et al. |
| 2008/0221672 | A1 | 9/2008 | Lamphere et al. |
| 2008/0243245 | A1 | 10/2008 | Thambar et al. |
| 2008/0269878 | A1 | 10/2008 | Iobbi |
| 2009/0005863 | A1 | 1/2009 | Goetz et al. |
| 2009/0076598 | A1 | 3/2009 | Salahieh et al. |
| 2009/0138079 | A1 | 5/2009 | Tuval et al. |
| 2009/0248132 | A1 | 10/2009 | Bloom et al. |
| 2009/0248133 | A1 | 10/2009 | Bloom et al. |
| 2009/0264997 | A1 | 10/2009 | Salahieh et al. |
| 2009/0287299 | A1 | 11/2009 | Tabor et al. |
| 2009/0306768 | A1 | 12/2009 | Quadri |
| 2010/0036479 | A1 | 2/2010 | Hill et al. |
| 2010/0082089 | A1 | 4/2010 | Quadri et al. |
| 2010/0082094 | A1 | 4/2010 | Quadri et al. |
| 2010/0298931 | A1 | 11/2010 | Quadri et al. |
| 2011/0022157 | A1 | 1/2011 | Essinger et al. |

FOREIGN PATENT DOCUMENTS

| | | |
|---|---|---|
| WO | WO 01/35870 | 5/2001 |
| WO | WO 03/092554 | 11/2003 |
| WO | WO 2005/011534 | 2/2005 |
| WO | WO 2005/087140 | 9/2005 |
| WO | WO 2007/123658 | 11/2007 |
| WO | WO 2008/091515 | 7/2008 |

OTHER PUBLICATIONS

PCT; International Search Report for PCT/US2006/043526; May 24, 2007.

* cited by examiner

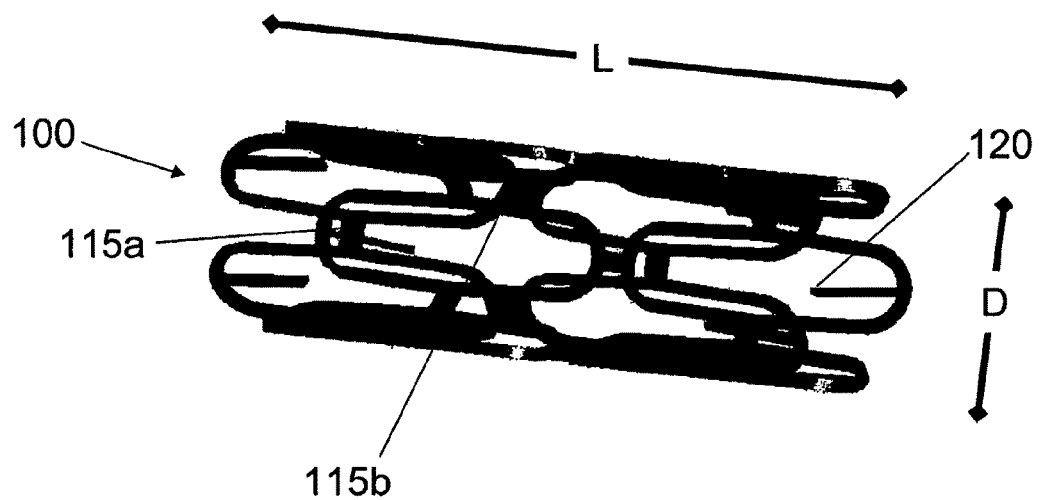
FIGURE 3
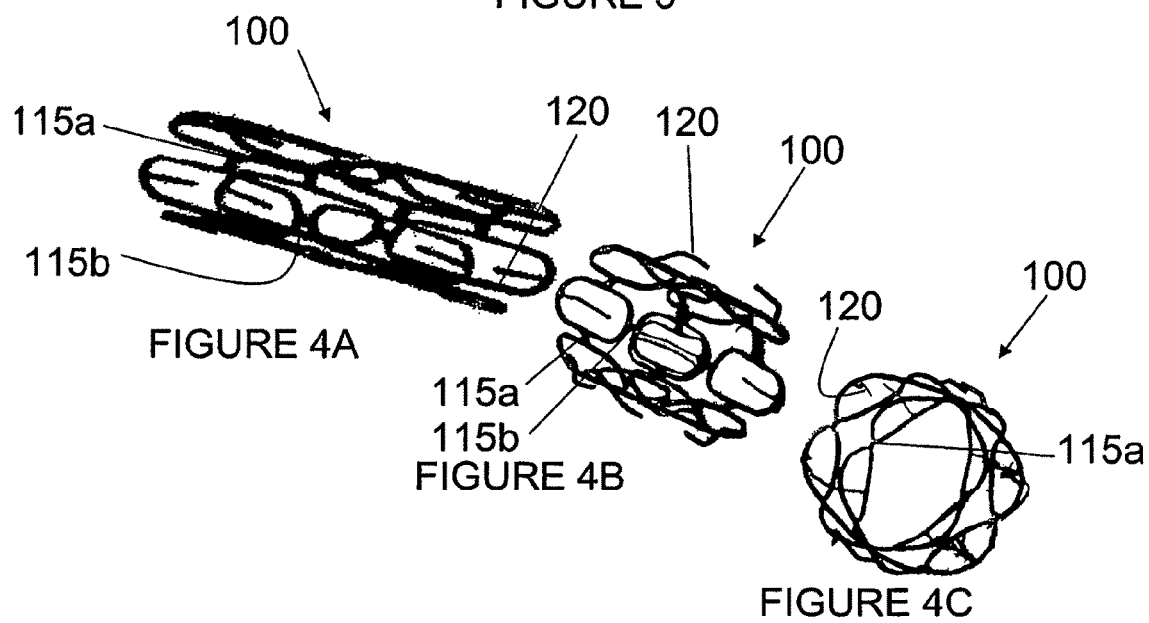
FIGURE 4A
FIGURE 4B
FIGURE 4C

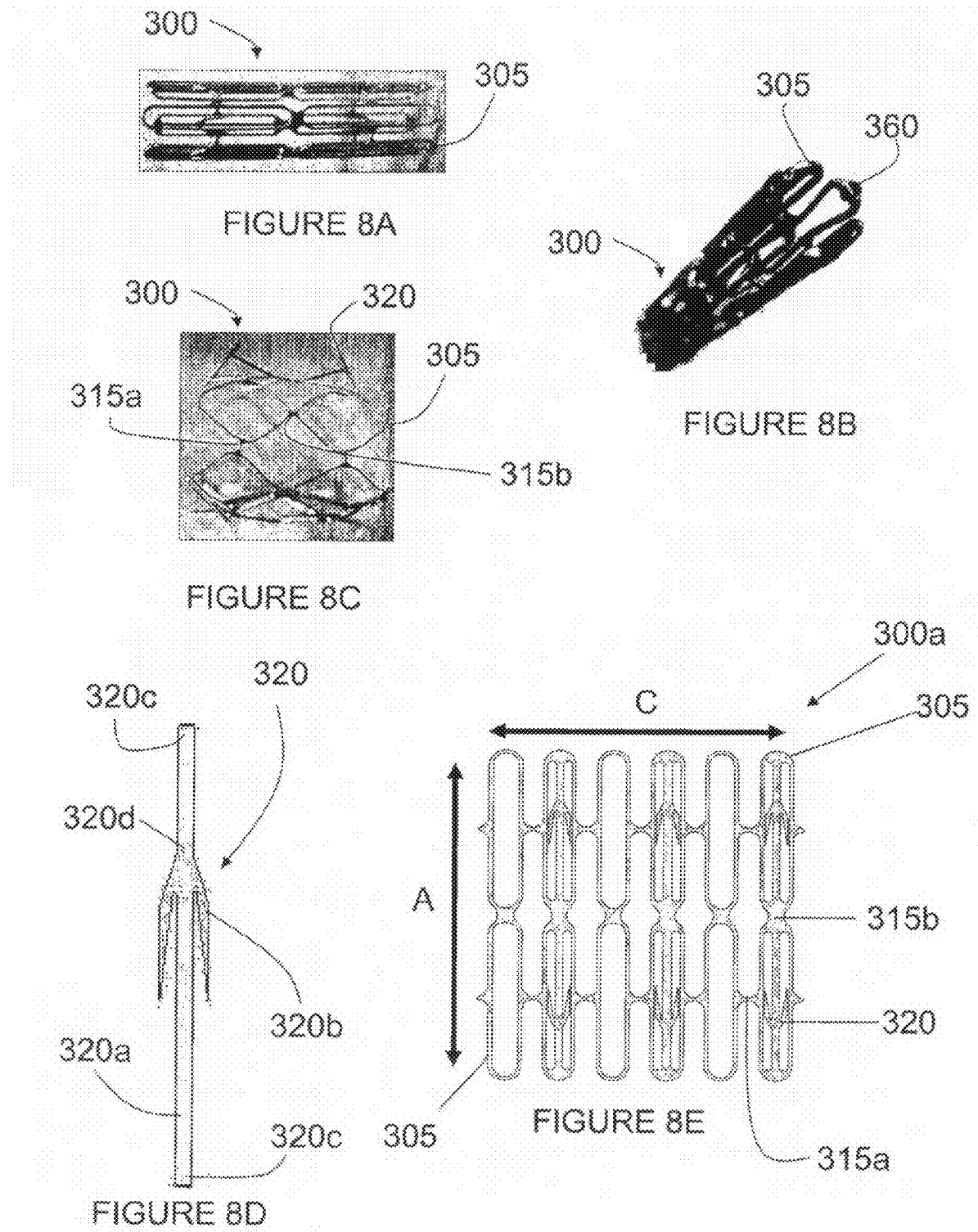

VASCULAR PROSTHESIS CONNECTING STENT

This is a national stage of PCT/US2006/043526 filed Nov. 9, 2006 and published in English, claiming benefit of U.S. Provisional Application No. 60/735,221, filed Nov. 10, 2005.

BACKGROUND OF THE INVENTION

Field of the Invention

The present invention relates to a vascular balloon-expandable and/or self-expanding stent that can be used as a connecting/attaching mechanism for various kinds of vascular grafts or other prostheses in the vascular system of the human body

SUMMARY OF THE INVENTION

It is a primary object of the present invention to provide a vascular balloon-expandable and/or self-expanding stent to facilitate efficient execution of simple and more complex vascular and cardiac procedures by less invasive and/or percutaneous techniques.

This and other objects of the present invention are achieved by an expandable vascular stent comprising an m×n array of ovals formed into a cylinder having a diameter, a circumference, an axis, and a length in the direction of the axis, where m is the number of columns of ovals in the circumferential direction and n is the number of rows of ovals in the axial direction. Connecting means located at rows 1 and n of the m×n array connect the cylinder to a surrounding body. The array of ovals can be of any size and number in a given stent.

The ovals have a short axis and a long axis, the short axis of the ovals extending in the circumferential direction and the long axis of the ovals extending in the axial direction. The cylinder is expandable from an initial diameter to a predetermined final diameter, wherein an increase in the diameter of the stent results in a substantial decrease in the length of the stent to bring the prongs together to produce a connection to the body surrounding the stent.

The connecting means comprise a plurality of prongs extending inwardly from the outer ends of respective ovals in rows 1 and n of the m×n array. The prongs are arranged in facing pairs extending from ovals that are in alignment in the axial direction, and are approximately collinear in ovals having a common long axis, and approximately parallel in ovals having a common short axis.

Prior to expansion of the cylinder, the prongs substantially conform to the shape of the cylinder. As the stent expands, the distance between the prongs decreases and the prongs extend outwardly from the cylinder to engage the surrounding tissue.

Circumferential connectors connect adjacent ovals to each other in the circumferential direction and axial connectors connecting adjacent ovals to each other in the axial direction. The circumferential connectors and the axial connectors are positioned between the ovals coincident with the common short and long axes of the ovals, respectively.

The tube and the prongs can be made of surgical stainless steel, the tube being expandable using an angioplasty balloon; or the tube and the prongs can be made of a memory metal and the tube is self-expanding.

Other objects, features, and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIG. 3 shows the stent form of FIG. 1 rolled into a stent.

FIGS. 4A-4C show the progression of deformation of the stent of FIG. 3 as it is stretched radially along its diameter.

FIG. 8A is a side elevational view of a third embodiment of the stent.

FIG. 8B is a perspective view of the stent of FIG. 8A

FIG. 8C is a side elevational view of the stent of FIG. 8A in a deformed state after being stretched radially along its diameter.

FIG. 8D is an enlarged view of a prong of the stent of FIG. 8A.

FIG. 8E is a plan view of the stent form of FIG. 8A

DETAILED DESCRIPTION OF THE PREFERRED EMBODIMENTS

Figure 1:
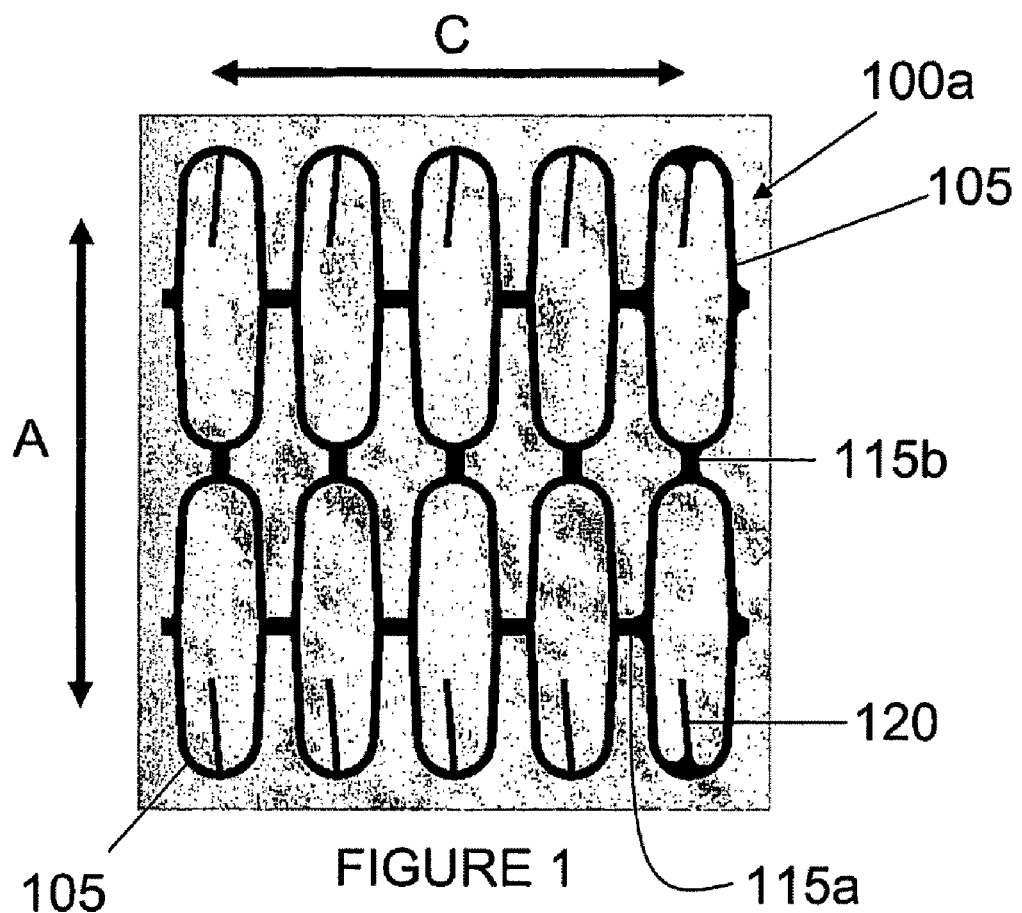
FIG. 1 shows a first embodiment of a stent form stamped from a piece of metal.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

As shown in FIGS. 3 and 4A-4C, a first embodiment of the device is a balloon expandable stainless steel stent 100 that can be expanded from an initial diameter (shown in FIG. 4A) to a pre-determined final diameter (shown in FIG. 4C) depending on the set dimensions of the balloon used to expand it. The configuration of the stent 100 is such that, with reference to FIG. 3, an increase in the diameter (D) of the stent will result in a substantial decrease in the length (L) of the stent.

To achieve this change in the shape and dimension of the stent 100, an m×n array 100a of ovals 105 is formed as shown in FIG. 1, where m is the number of columns of ovals in the circumferential direction C and n is the number of rows of ovals in the axial, or lengthwise, direction A, and where the short axis of the ovals 105 extends in the circumferential direction C and the long axis of the ovals 105 extends in the axial direction A. The array 100a shown in FIG. 1 is a 2×5 array. However, the array 100a can be any size greater than 1×1, depending on the desired size of the circumference and the length of the stent.

Figure 2:
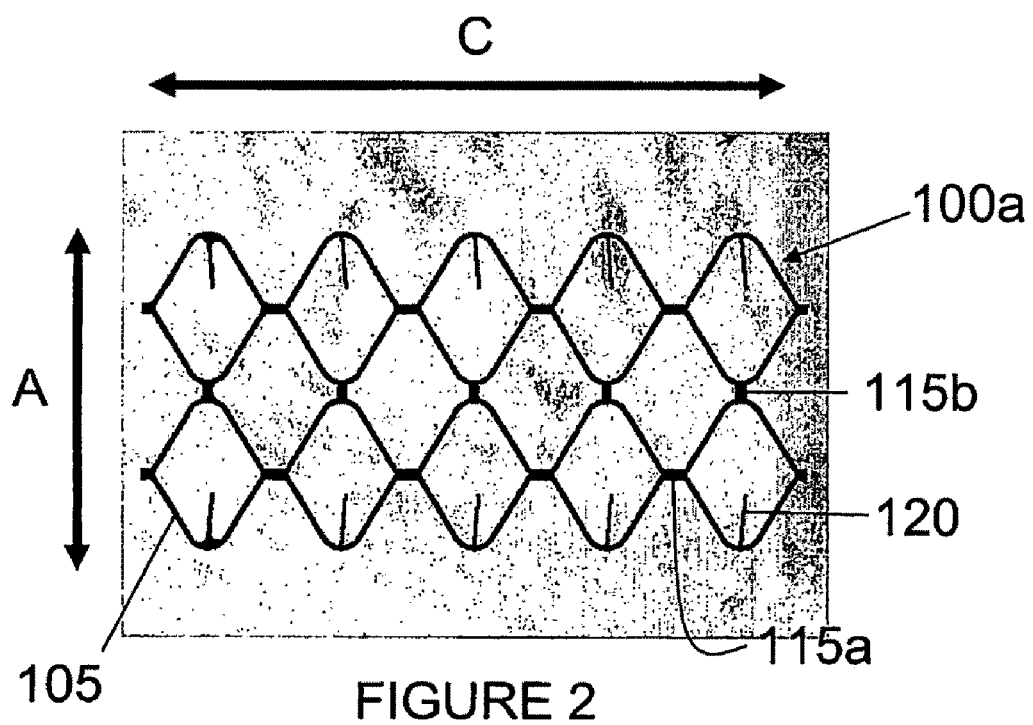
FIG. 2 shows the stent form of FIG. 1 stretched width-wise.

With reference to FIGS. 1 and 2, the array 100a of ovals 105 can be formed by stamping or electrical discharge machining from a sheet or tube of metal, preferably stainless steel. Adjacent ovals 105 are connected to each other in the circumferential direction C by connectors 115a and in the axial direction A by connectors 115b positioned between the ovals coincident with their common short and long axes, respectively.

At least some of the ovals 105 at the ends of the stent 100 (that is, the ovals 105 in rows 1 and n in the axial direction) have a prong 120 extending inwardly from their outer ends in approximate alignment with their longitudinal axes. The prongs 120 are placed in facing pairs extending from ovals 105 that are in alignment in the axial direction A. Thus, for ovals 105 having a common long axis, the prongs 120 are approximately collinear; while for ovals 105 having a common short axis, the prongs 120 are approximately parallel.

There may be intervening "blank" ovals 105 without any prongs 120, and which serve merely as spacers. The blank ovals 105 are utilized in some situations where more space is required between the connecting prongs 120.

If the array 100a of ovals 105 is formed from a sheet of metal, then the array 100a is rolled into a cylinder. The rolled cylinder and the stamped or machined tube have the general configuration of a stent 100, as shown in FIG. 4A, with the longitudinal axis of the cylinder being parallel to the long axes of the ovals 105.

In this embodiment, the prongs 120 are pre-bent. That is, at the time the stent 100 is formed, the prongs 120 are bent outwardly relative to the longitudinal axis of the cylinder, adjacent their attached ends, and also are bent inwardly relative to the longitudinal axis of the cylinder at a point offset from their free ends, in a reverse curve, so as to have a hook configuration.

An angioplasty balloon 130 is used to expand the undeployed stent 100 and to post the expanded stent 100 in the wall of an artery or other body cavity. When the balloon 130 is inflated, the ovals 105 expand in the direction of their short axes and contract along the direction of their long axes, deforming the ovals 105 into diamonds and causing a reduction in the length of the stent 100, as shown in FIGS. 4B and 4C. As also shown in FIGS. 4B and 4C, the deformation of the ovals 105 also causes the approximately collinear prongs 120 to draw closer together to engage the surrounding tissue and the approximately parallel prongs 120 to spread farther apart. This deformation of the ovals 105 and movement of the prongs 120 provide the connecting mechanism of the stent 100.

The angioplasty balloon 130 is the correct size and shape to expand the stent 100 to the desired size and shape. The undeployed stent 100 is loaded over the balloon 130 of a conventional balloon catheter 132 and inserted into the artery or other body cavity according to conventional medical procedure. Inflating the balloon 130 deploys (opens) the stent 100 (that is, causes an increase in its diameter and a decrease in its length), which remains expanded to keep the artery or body cavity open. A high-pressure balloon 130 allows the physician to fully expand the stent 100 until it is in full contact with the wall of the artery or other body cavity. A low compliance balloon 130 is used so that the stent 100 and the artery or body cavity will not be over-expanded, and so that the balloon 130 will not dog-bone and over-expand the artery or body cavity on either end of the stent 100. The stent 100 stays in position after the balloon 130 is deflated and removed from the body.

In instances when the stent 100 is self-expanding, i.e. made from memory metal, then upon deployment the stent 100 takes its predetermined configuration.

Figure 5A:
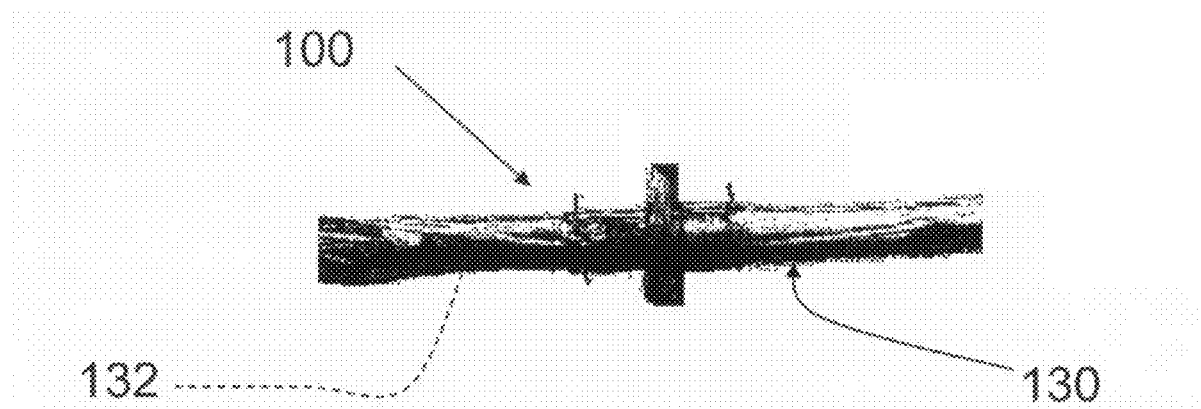
FIGS. 5A-5Q show the steps in the expansion of the stent of FIG. 3 in an artery or other body cavity.
Figure 5B:
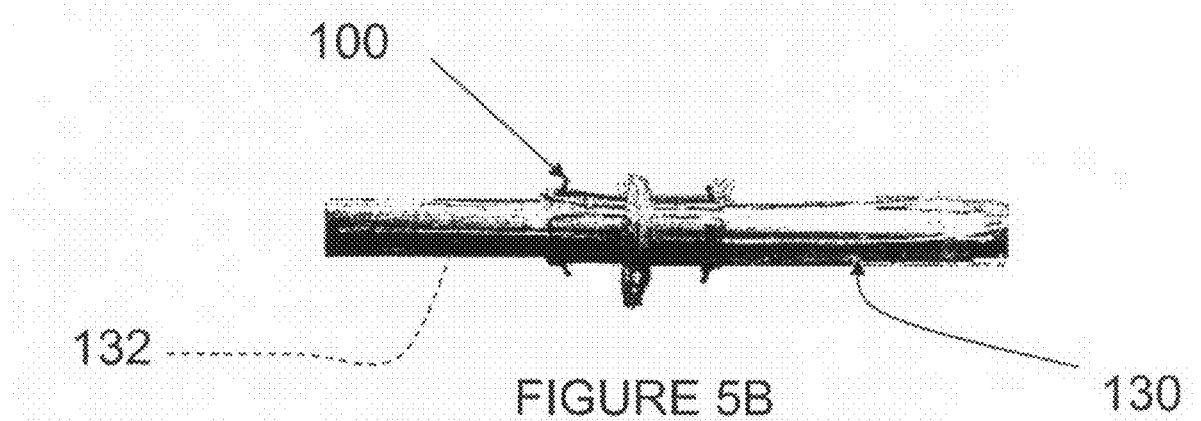
Figure 5C:
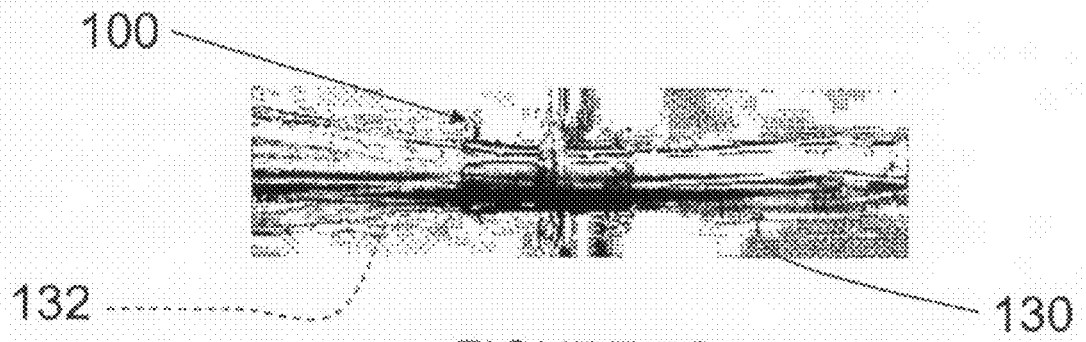
Figure 5D:
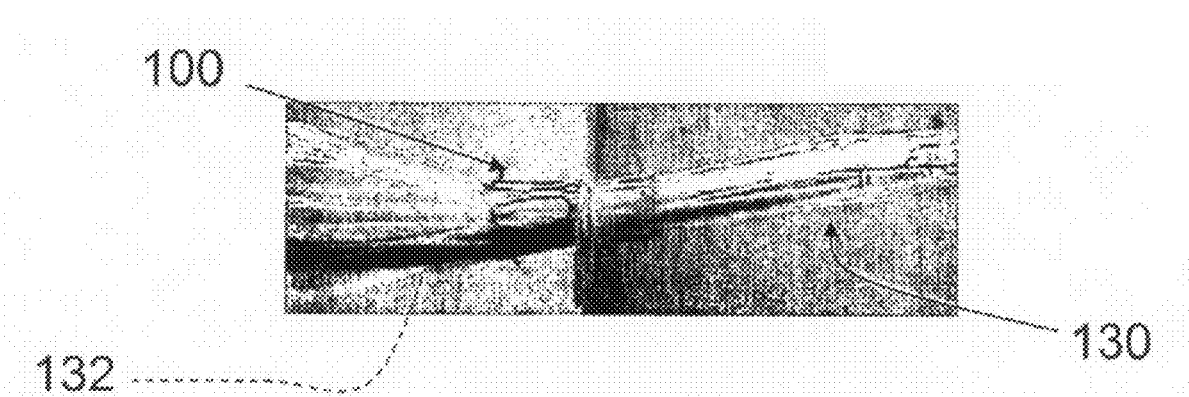
Figure 5E:
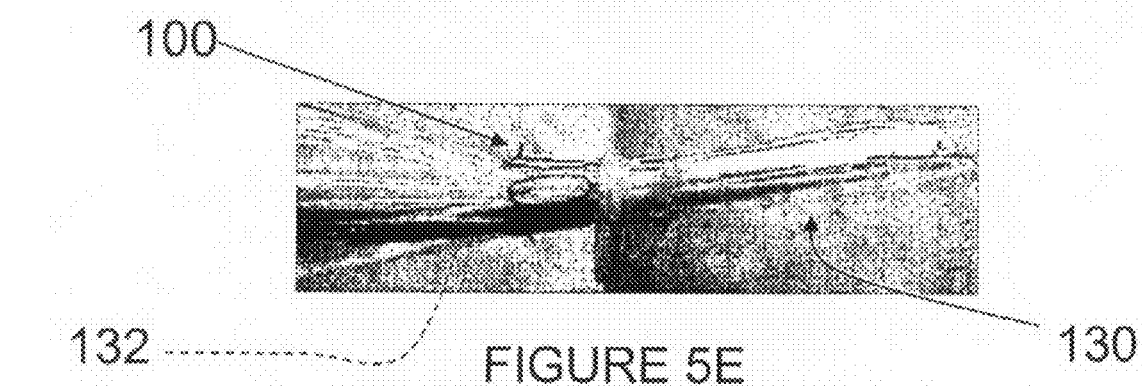
Figure 5F:
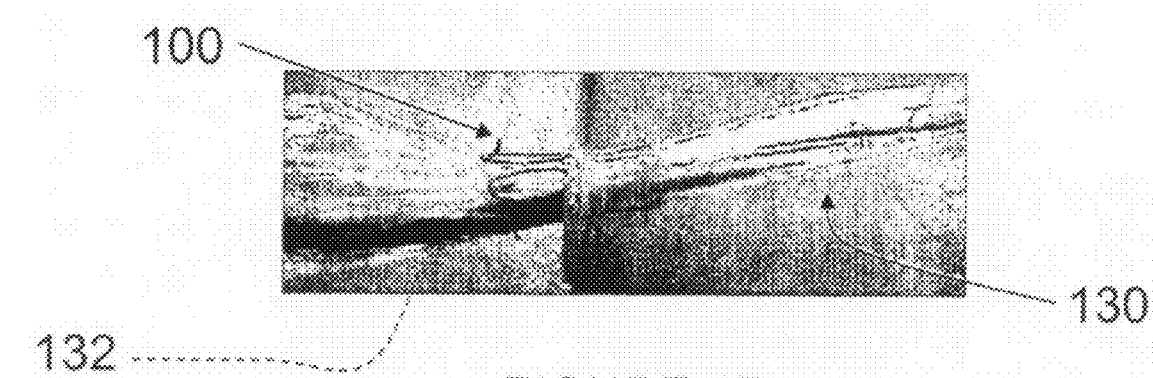
Figure 5G:
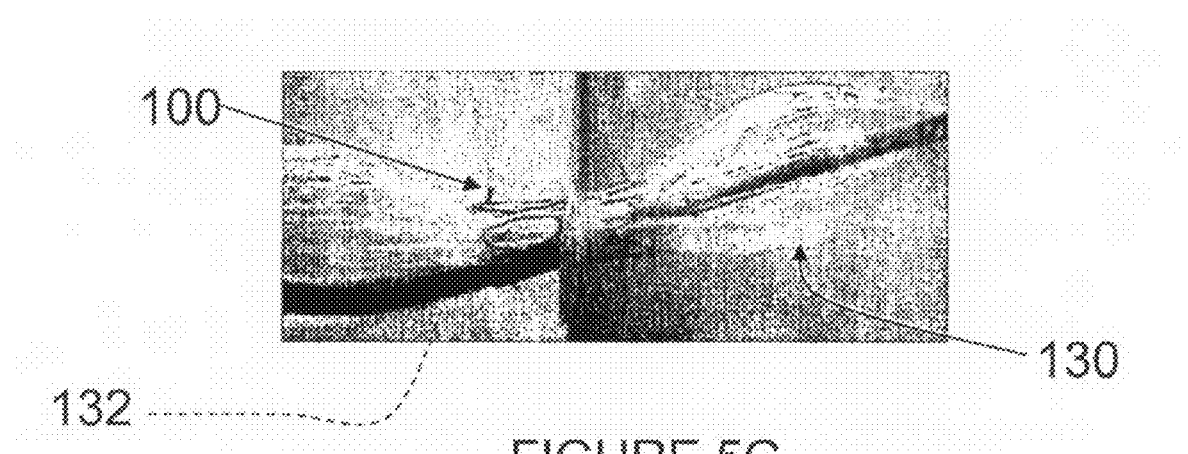
Figure 5H:
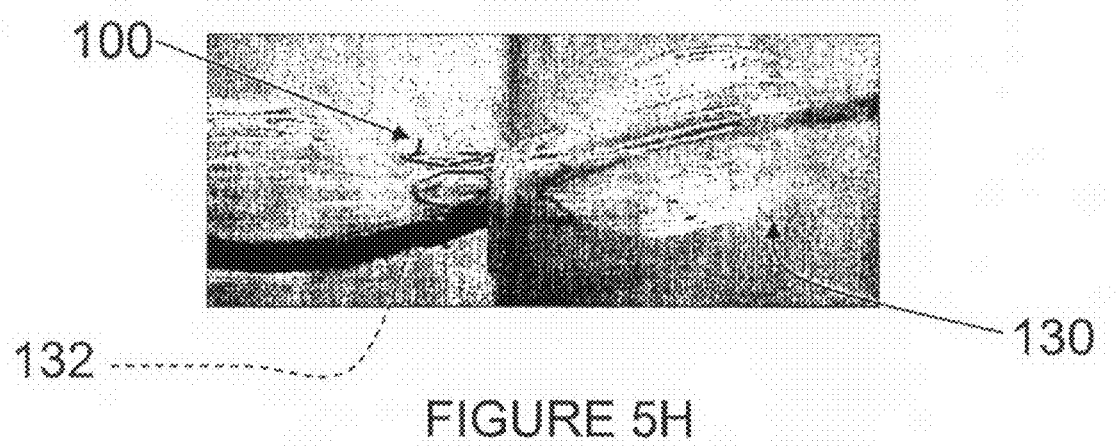
Figure 5I:
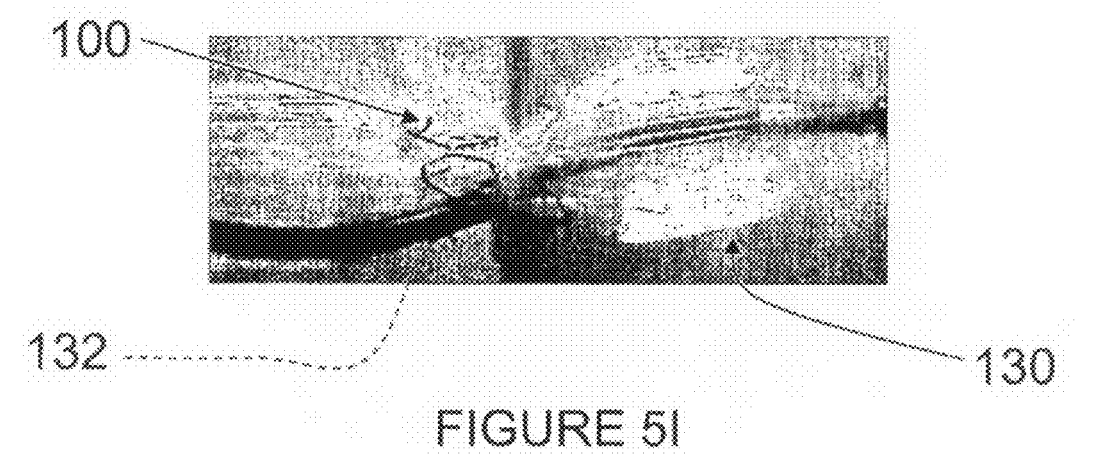
Figure 5J:
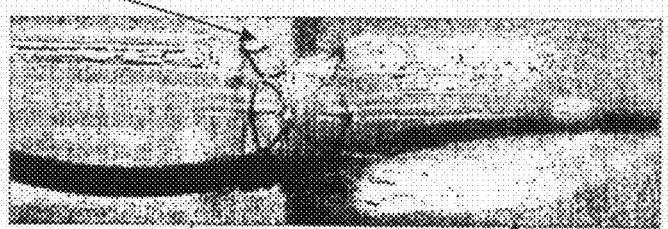
Figure 5K:
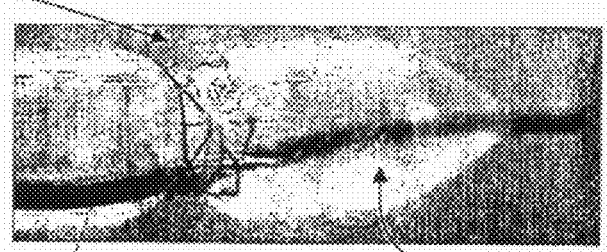
Figure 5L:
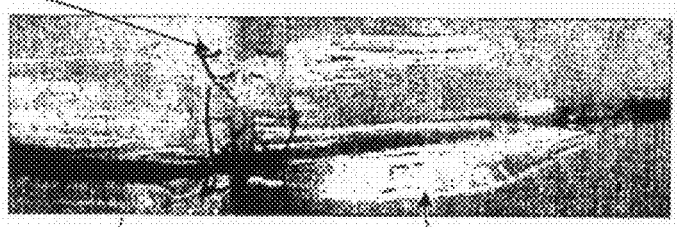
Figure 5M:
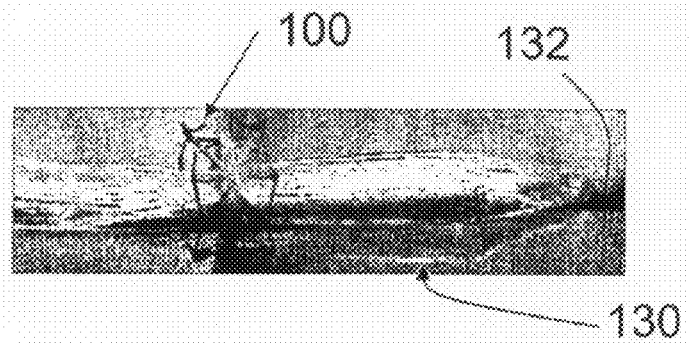
Figure 5N:
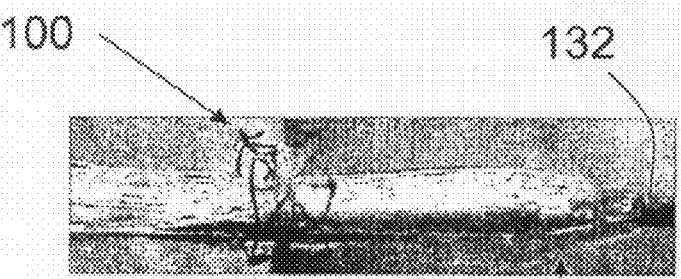
Figure 5O:
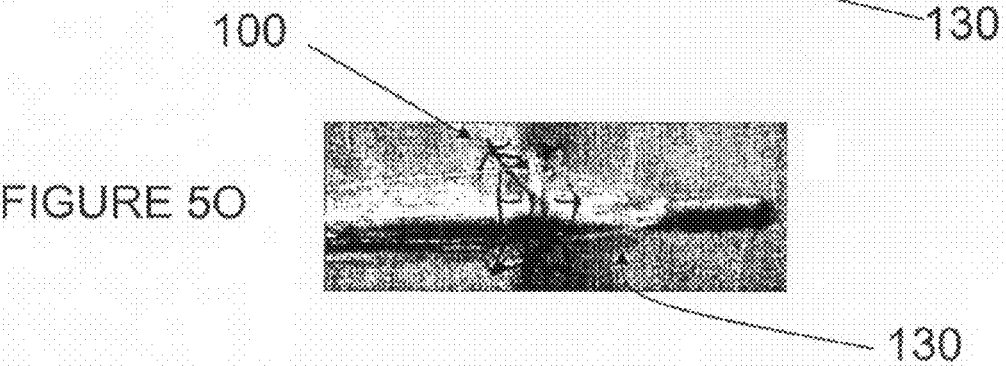
Figure 5P:
Figure 5Q:
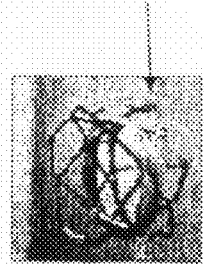

FIGS. 5A-5Q show the steps in the expansion of the stent of FIG. 3 in an artery or other body cavity.

The stent 100 in accordance with the present invention can also be of use as a versatile connector in clinical settings in which it can be pre-attached to a side wall of another prosthesis, such as an endo-luminal graft. It can also be used as a connector to connect main and branch endo-aortic grafts for branch graft repair, as described in my co-pending U.S. patent application Ser. No. 10/960,296, filed Oct. 8, 2004.

The stent 100 in accordance with the present invention can further be used in conjunction with percutaneous heart valve technology. In a percutaneous heart valve procedure, a collapsed percutaneous heart valve 125 is mounted on a balloon-expandable stent 100 and threaded through the patient's circulatory system via a catheter to the aortic valve from either an antegrade approach (in which the patient's septum and mitral valve are crossed to reach their native aortic valve) or a retrograde approach (in which the percutaneous heart valve 125 is delivered directly to the aortic valve through the patient's main artery). Once in the aortic valve, the percutaneous heart valve 125 is expanded by a balloon catheter to push the patient's existing valve leaflets aside and anchor inside the valve opening.

Figure 6A:
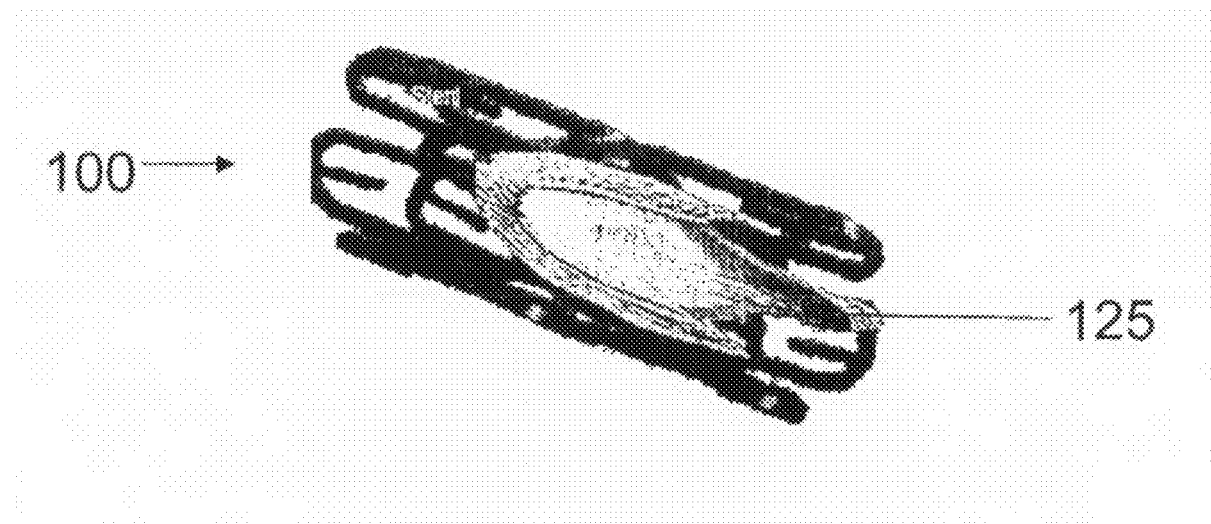
FIG. 6A is a perspective view, partially cut away, of a collapsed prosthetic heart valve loaded in an undeployed stent in accordance with the present invention.
Figure 6B:
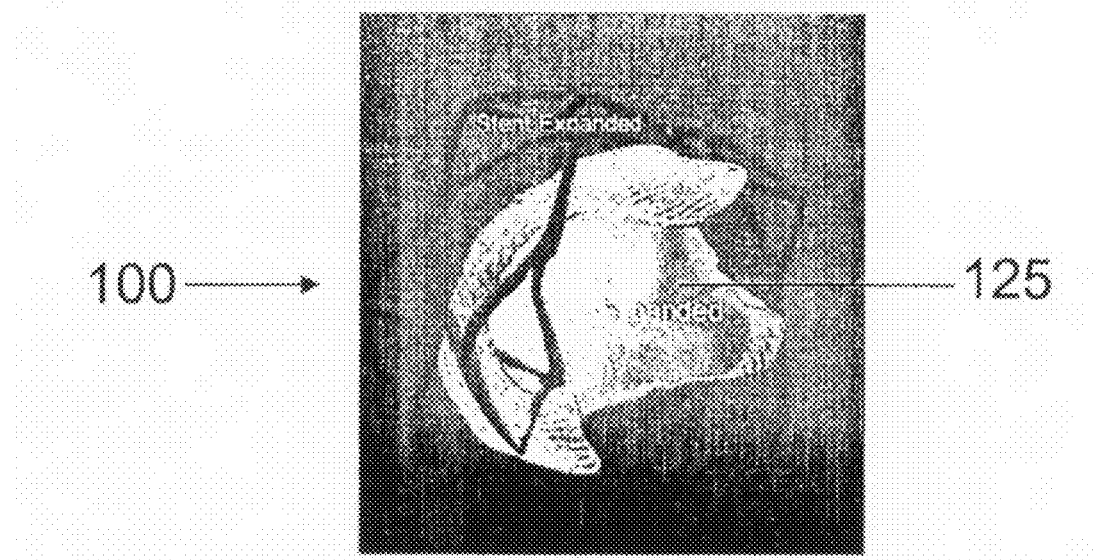
FIG. 6B is a perspective view, partially cut away, of the prosthetic heart valve and stent of FIG. 6A in their expanded conditions.

As shown in FIG. 6A, the percutaneous heart valve 125 in a collapsed state can be seated inside the undeployed stent 100 in accordance with the present invention, which in turn is loaded over the balloon of a conventional balloon catheter, as previously described. Once the valve 125 and stent 100 are positioned in the desired location, the balloon 130 is inflated, causing the valve 125 and the stent 100 to expand, as shown in FIG. 6B. The valve 125 is fixed in position by the mechanism provided by the stent 100.

Figure 7A:
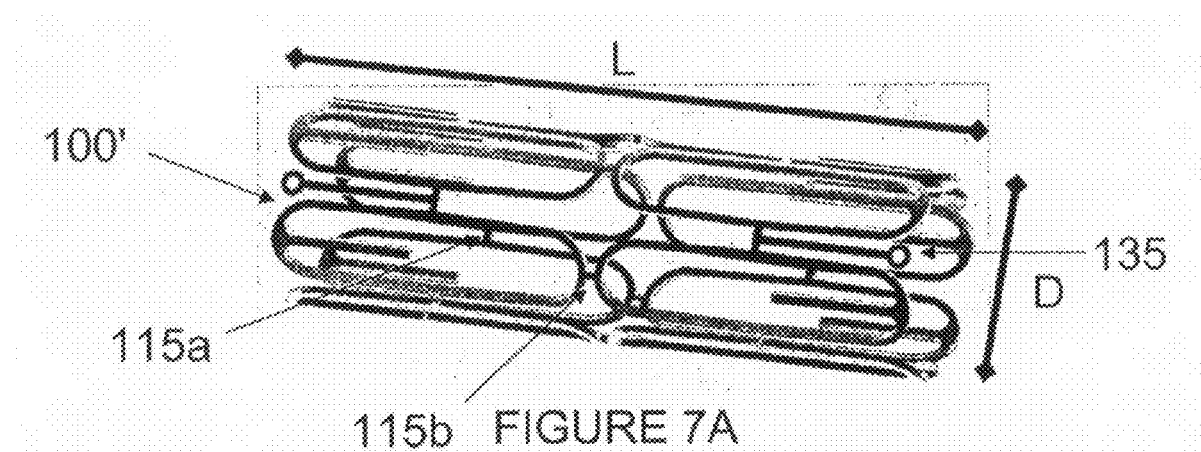
FIGS. 7A-7C show the progression of deformation of a second embodiment of the stent as it is stretched radially along its diameter.
Figure 7B:
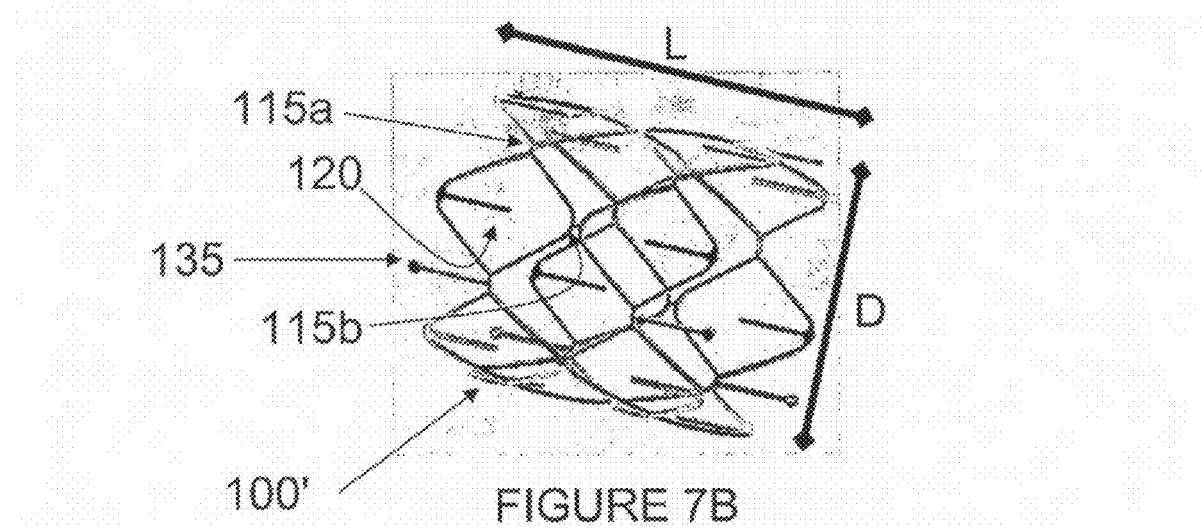
Figure 7C:
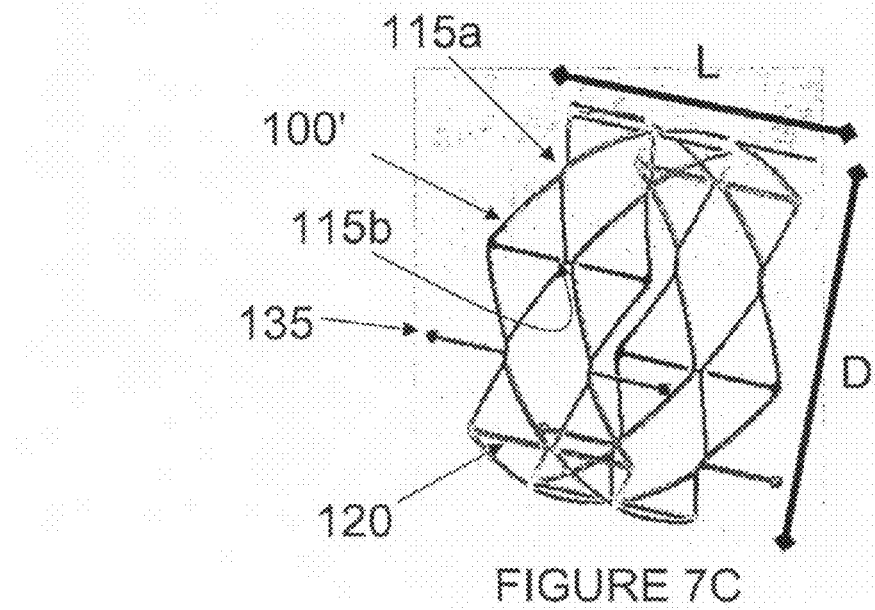

A second embodiment of the stent 100', and the progression of its deformation as it is stretched radially along its diameter, is shown in FIGS. 7A-7C. In this alternate embodiment, the stent 100' is similar to the stent 100, but has additional prongs 135 extending from and perpendicular to the connectors 115a positioned between the ovals 105, and parallel to the longitudinal axis of the stent 100'. These prongs 135 are for the purpose of attaching the stent 100' to, for example, a branch graft or a valve.

A third embodiment of the stent 300 is shown in its undeployed state in FIGS. 8A and 8B, and in its deployed state after being stretched radially along its diameter in FIG. 8C. In the third embodiment, the stent 300 is formed of an m×n array 300a of ovals 305 formed as shown in FIG. 8E. With reference to FIG. 8D, the array 300a of ovals 305 can be formed by laser-cutting a sheet or tube of metal, preferably stainless steel or a memory metal. Adjacent ovals 305 are connected to each other in the circumferential direction C by connectors 315a and in the axial direction A by connectors 315b positioned between the ovals coincident with their common short and long axes, respectively.

At least some of the ovals 305 at the ends of the stent 300 (that is, the ovals 305 in rows 1 and n in the axial direction) have a prong 320 extending inwardly from their outer ends in approximate alignment with their longitudinal axes. The prongs 320 are placed in facing pairs extending from ovals 305 that are in alignment in the axial direction A. Thus, for ovals 305 having a common long axis, the prongs 320 are approximately collinear; while for ovals 305 having a common short axis, the prongs 320 are approximately parallel. The prongs 350 are bifurcated, providing two point penetration for better purchase.

Referring now to FIGS. 8D and 8E, in the embodiment of FIGS. 8A-8C, each prong 320 includes a spine 320a extending the length of the long axis of the oval 305 and a furcation 320b on either side of the spine 320a at a location between the ends of the spine 320. The spine 320a has two end hinge points 320c at the ends thereof and one intermediate hinge point 320d at the base of the furcations 320b. The amount by which the ovals 305 are foreshortened and the angle of the prongs 320 (that is, the angle of the furcations 320b) can be adjusted by varying the location of the furcations 320b and the intermediate hinge point 320d relative to the ends of the spines 320 and the end hinge points 320c.

There may be intervening "blank" ovals 305 without any prongs 320, and which serve merely as spacers. The blank ovals 305 are utilized in some situations where more space is required between the connecting prongs 320. At least some of the ovals 305 at one end of the stent 300 can include a docking socket 360 (shown in FIG. 8C) for mating to the cardiac locking pin of a valve frame.

Figure 9A:
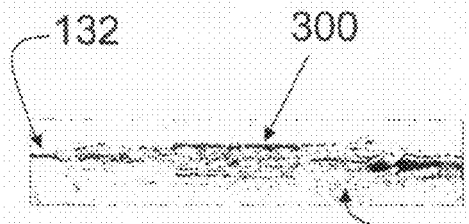
FIGS. 9A-9G show the steps in the expansion of the stent of FIG. 8A in an artery or other body cavity.
Figure 9B:
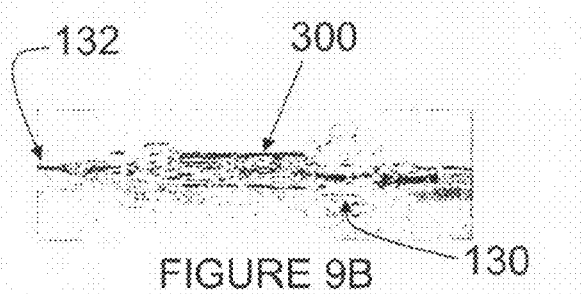
Figure 9C:
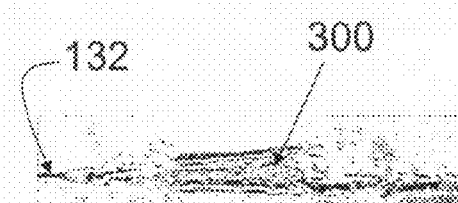
Figure 9D:
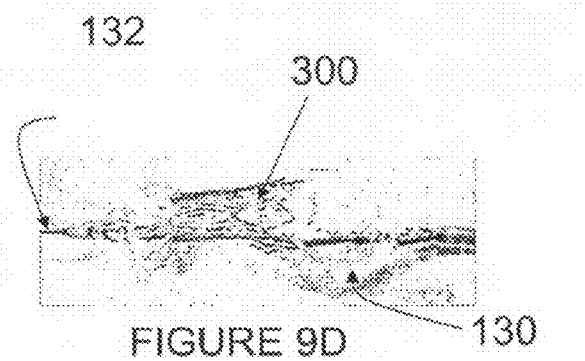
Figure 9E:
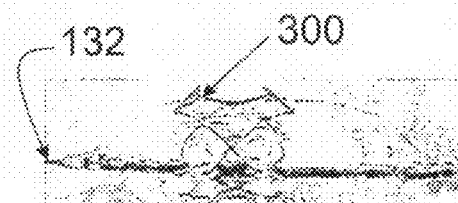
Figure 9F:
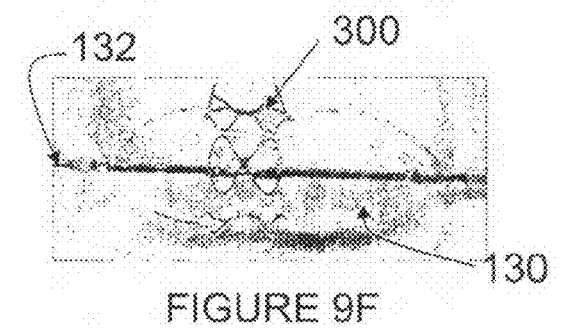
Figure 9G:
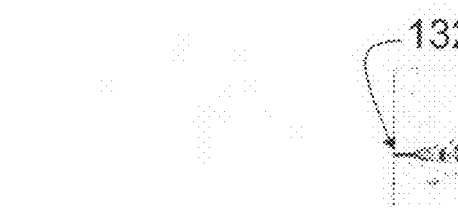

FIGS. 9A-5Q show the steps in the expansion of the stent of FIGS. 8A-8C in an artery or other body cavity, using an angioplasty balloon. The undeployed stent 300 is loaded over the balloon 130 of a conventional balloon catheter 132 and inserted into the artery or other body cavity according to conventional medical procedure. As the balloon 130 inflates, the ovals 305 foreshorten in the axial direction, causing the spines 320a of the prongs 320 to bend at the hinges 320c and 320d and the consequent activation of the prongs 320. As the balloon 130 continues to inflate, the angles assumed by the spines 320a at their hinges reach their maximums, bringing opposing furcations 320b together to engage the tissue therebetween.

Figure 10A:
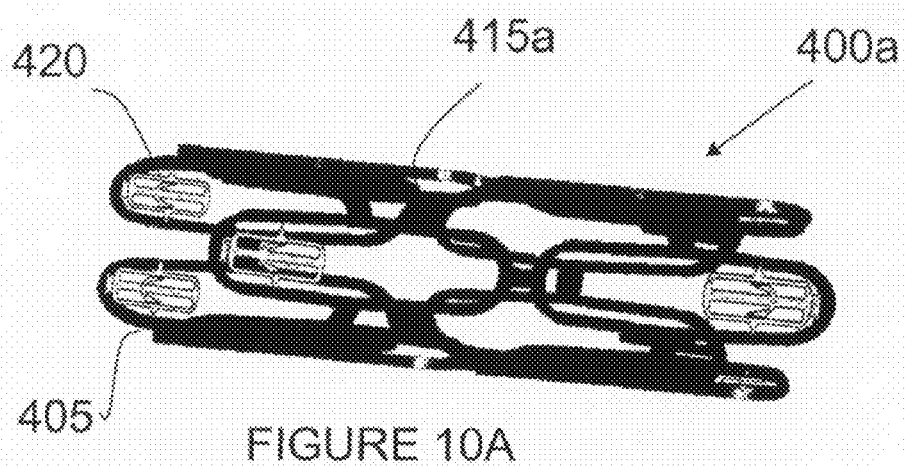
FIG. 10A is a perspective view of a fourth embodiment of the stent.
Figure 10B:
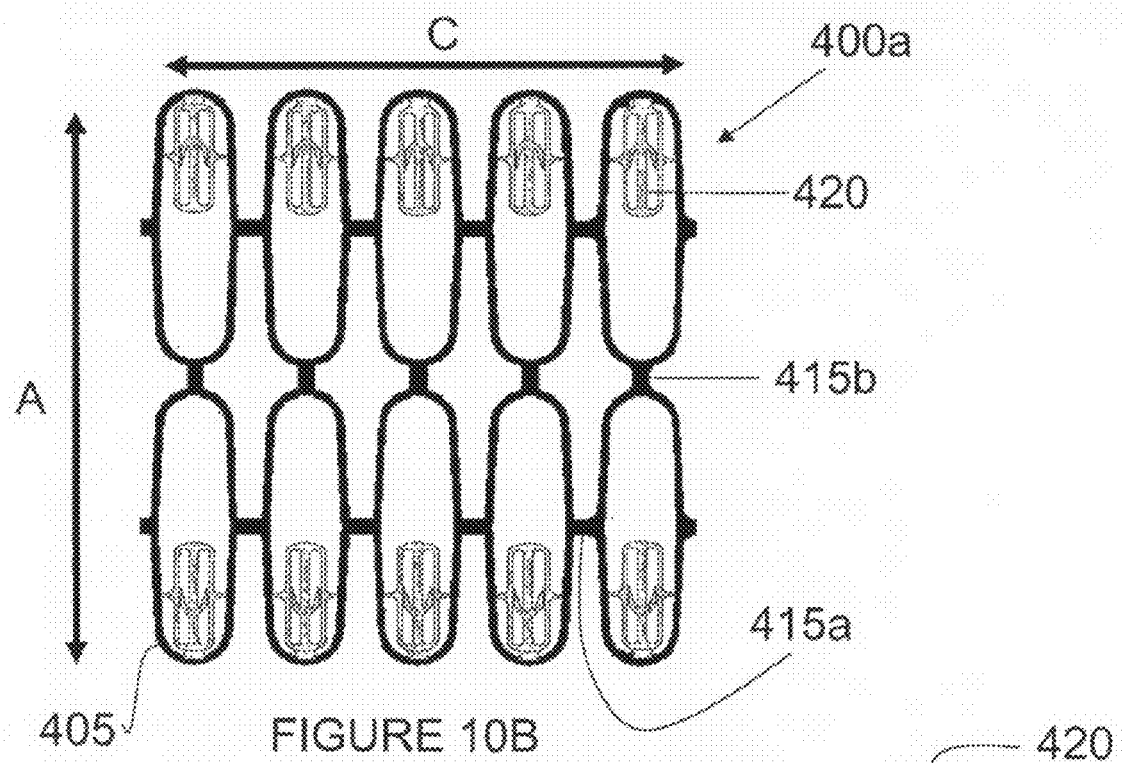
FIG. 10B is a plan view of the stent form of FIG. 10A.

Referring now to FIGS. 10A and 10B, there is shown a fourth embodiment of the stent 400. In the fourth embodiment, the stent 400 is formed of an m×n array 400a of ovals 405. With reference to FIG. 10B, the array 400a of ovals 405 can be formed by laser-cutting a sheet or tube of metal, preferably stainless steel. Adjacent ovals 405 are connected to each other in the circumferential direction C by connectors 415a and in the axial direction A by connectors 415b positioned between the ovals coincident with their common short and long axes, respectively.

At least some of the ovals 405 at the ends of the stent 400 (that is, the ovals 405 in rows 1 and n in the axial direction) have a prong 420 extending inwardly from their outer ends in approximate alignment with their longitudinal axes. The prongs 420 are placed in facing pairs extending from ovals 405 that are in alignment in the axial direction A.

Figure 10C:
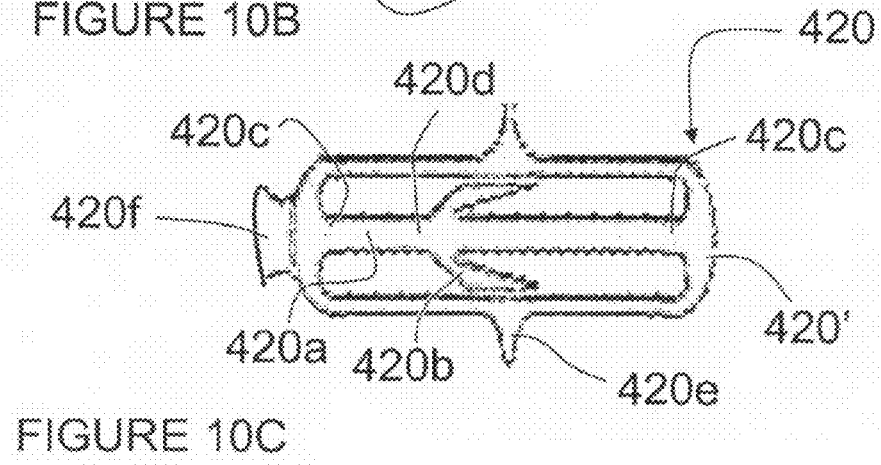
FIG. 10C is an enlarged view of the prong of the stent of FIG. 10A.

As shown in FIG. 10C, each prong 420 has substantially the same configuration as an oval 305 and a prong 320 of the third embodiment, described above. That is, each prong 420 includes an oval frame 420', a spine 420a extending the length of the long axis of the oval frame 420', and a furcation 420b on either side of the spine 420a at a location between the ends of the spine 420. The spine 420a has two end hinge points 420c at the ends thereof and one intermediate hinge point 420d at the base of the furcations 420b.

The oval frames 420' are connected at their short axes to the ovals 405 by connectors 420e, and are connected at one end of their long axes to the ovals 405 by a connector 420f. Thus, as the ovals 405 foreshorten, the oval frames 420' also foreshorten. The amount by which the oval frames 420' are foreshortened and the angle of the furcations 420b can be adjusted by varying the location of the furcations 420b and the intermediate hinge point 420d relative to the ends of the spines 420 and the end hinge points 420c. Preferably, the prongs 420 are formed by laser cutting.

As with stent 300, stent 400 is loaded over the balloon 130 of a conventional balloon catheter 132 and inserted into the artery or other body cavity according to conventional medical procedure. As the balloon 130 inflates, the ovals 405 and the oval frames 420' foreshorten in the axial direction, causing the spines 420a of the prongs 420 to bend at the hinges 420c and 420d and the consequent activation of the prongs 420. As the balloon 130 continues to inflate, the angles assumed by the spines 420a at their hinges reach their maximums, bringing opposing furcations 420b together to engage the tissue therebetween.

There may be intervening "blank" ovals 405 without any prongs 420, and which serve merely as spacers. The blank ovals 405 are utilized in some situations where more space is required between the connecting prongs 420. At least some of the ovals 405 at one end of the stent 400 can include a docking socket (not shown) similar to the docking socket 360 shown in FIG. 8C, for mating to the cardiac locking pin of a valve frame.

Modifications and variations of the above-described embodiments of the present invention are possible, as appreciated by those skilled in the art in light of the above teachings. It is therefore to be understood that the invention may be practiced otherwise than as specifically described.

What is claimed is:

1. An expandable vascular stent comprising
an m×n array of ovals formed in a cylinder having a diameter, a circumference, an axis, and a length in the direction of the axis, where m is the number of columns of ovals in the circumferential direction and n is the number of rows of ovals in the axial direction, the ovals having a short axis and a long axis, the short axis of the ovals extending in the circumferential direction and the long axis of the ovals extending in the axial direction, the cylinder being expandable from an initial diameter to a pre-determined final diameter, wherein an increase in the diameter of the stent results in a decrease in the length of the stent; and
a plurality of prongs located at rows 1 and n of the m×n array for connecting the cylinder to a surrounding body, a first plurality of prongs located at row 1 extending generally radially outwardly from the ovals and generally toward a second plurality of prongs located at row n, and the second plurality of prongs located at row n extend generally radially outwardly from the ovals and generally toward the first plurality of prongs at row 1;
wherein when the stent is expanded to the final diameter, each of the prongs is bent at or adjacent the ovals so that an elongate first portion along the length of the prong extends radially outwardly, and each of the prongs is further bent radially inwardly relative the first portion so that an elongate second portion along the length of the prong is spaced radially outwardly from the ovals and extends in a generally axial direction.

2. The expandable vascular stent of claim 1, wherein prongs from the first plurality of prongs are arranged in facing pairs with prongs from the second plurality of prongs when the respective prongs extend from ovals that are in alignment in the axial direction.

3. The expandable vascular stent of claim 2, wherein when the stent is expanded to the final diameter, the elongate second portions of the prongs in facing pairs are approximately collinear.

4. The expandable vascular stent of claim 2, wherein prior to expansion of the cylinder, the prongs substantially conform to the shape of the cylinder and after expansion, the prongs extend outwardly, from the cylinder to engage the surrounding body.

5. The expandable vascular stent of claim 1, further comprising circumferential connectors connecting adjacent ovals to each other in the circumferential direction and axial connectors connecting adjacent ovals to each other in the axial direction.

6. The expandable vascular stent of claim 5, wherein the circumferential connectors and the axial connectors are positioned between the ovals coincident with the common short and long axes of the ovals, respectively.

7. The expandable vascular stent of claim 5, further comprising prongs extending from at least some of the circumferential connectors between ovals in rows 1 and n.

8. The expandable vascular stent of claim 1, wherein on continued expansion at a desired location within a patient, due to foreshortening of the ovals tissue is engaged in between the prongs so as to form a stable connection of the stent to tissue at the desired location.

9. The expandable vascular stent of claim 8, wherein the prongs exert a generally longitudinally-directed force on the tissue engaged therebetween.

10. The expandable vascular stent of claim 1, wherein the cylinder and the prongs are made of surgical stainless steel and the cylinder is expanded using an angioplasty balloon.

11. The expandable vascular stent of claim 1, wherein the cylinder and the prongs are made of a memory metal and the cylinder is self-expanding.

12. The expandable vascular stent of claim 1, further comprising a percutaneous heart valve seated inside the cylinder.

13. An expandable vascular stent comprising:
an m×n array of ovals formed in a cylinder having a diameter, a circumference, an axis, and a length in the direction of the axis, where m is the number of columns of ovals in the circumferential direction and n is the number of rows of ovals in the axial direction, the ovals having a short axis and a long axis, the short axis of the ovals extending in the circumferential direction and the long axis of the ovals extending in the axial direction, the cylinder being expandable from an initial diameter to a pre-determined final diameter, wherein an increase in the diameter of the stent results in a decrease in the length of the stent; and
a plurality of prongs located at rows 1 and n of the m×n array for connecting the cylinder to a surrounding body, a first plurality of prongs located at row 1 extending generally radially outwardly from the ovals and generally toward a second plurality of prongs located at row n, and the second plurality of prongs located at row n extend generally radially outwardly from the ovals and generally toward the first plurality of prongs at row 1;
wherein each prong includes a spine extending the length of the long axis of the oval and a furcation on either side of the spine at a location between the ends of the spine.

14. The expandable vascular stent of claim 13, wherein the spine has end hinge points at the ends thereof and an intermediate hinge point at the base of the furcations, and wherein an amount by which the ovals are foreshortened and an angle of the furcations upon expansion depends on the location of the intermediate hinge point relative to the end hinge points.

15. A support for a vascular prosthesis, comprising:
at least one row of interconnected foreshortening cells extending circumferentially around a longitudinal axis of the support, each of the foreshortening cells having a circumferential axis in the circumferential direction and a long axis in the longitudinal direction, each foreshortening cell having a proximal end and a distal end, the support being expandable from a compacted diameter to an expanded diameter, the foreshortening cells being configured so that when the support is expanded from the compacted diameter to the expanded diameter, the circumferential axis of each foreshortening cell increases while simultaneously the long axis of each foreshortening cell decreases;
a plurality of elongate distal prongs extending from the distal ends of foreshortening cells in one of the at least one row of interconnected foreshortening cells, the elongate distal prongs extend generally radially outwardly from the foreshortening cells and generally axially toward the proximal end of the associated foreshortening cells, each distal prong having a first and a second portion along its length, the prong being bent between the first and second portions so that the second portion extends in a more axially-directed direction than the first portion; and
a plurality of elongate proximal prongs extending from the proximal ends of foreshortening cells in one of the at least one row of interconnected foreshortening cells, the elongate proximal prongs extending generally radially outwardly from the foreshortening cells and generally axially toward the distal end of the associated foreshortening cells so that a space is defined between tips of the proximal and distal prongs, each proximal prong having a first and a second portion along its length, the prong being bent between the first and second portions so that the second portion extends in a more axially-directed direction than the first portion;
wherein when the support is radially expanded a longitudinal distance between the tips of the proximal and distal prongs decreases.

16. The support of claim 15, wherein the foreshortening cells are defined by a plurality of interconnected struts.

17. The support of claims 15, wherein when the support is expanded in diameter a shape of each foreshortening cell changes.

18. The support of claim 17, wherein at a first stent diameter a first one of the foreshortening cells is oval-shaped, and at a second stent diameter the first foreshortening cell is diamond-shaped.

19. The support of claim 15, wherein the support comprises a plurality of rows of interconnected foreshortening cells, and the proximal prongs extend from a different row of interconnected foreshortening cells than do the distal prongs.

20. The support of claims 15, wherein in the expanded configuration, the second portion of each of the distal and proximal prongs is substantially straight, and the substantially straight second portion of one of the proximal prongs is generally collinear with the substantially straight second portion of one of the distal prongs.

21. The support of claims 20, wherein in the expanded configuration the substantially straight second portion of one of the proximal prongs is generally parallel to the substantially straight second portion of another of the proximal prongs.

22. The support of claims 21, wherein in the expanded configuration the substantially straight second portion of one of the proximal prongs is generally parallel to the substantially straight second portion of at least one of the distal prongs.

23. The support of claim 15, further comprising a percutaneous heart valve seated inside the support.

24. The support of claim 15, wherein the prongs are configured so that when the support is expanded from the compacted diameter to the expanded diameter so that the longitudinal distance between the tips of the proximal and distal prongs decreases, body tissue in the space between the tips of the proximal and distal prongs is engaged by the prongs sufficient to form a stable connection between the support and the tissue.

25. The support of claim 24, wherein the tips of the prongs exert a generally longitudinally-directed force on the tissue engaged therebetween.

26. The support of claim 25 in combination with an expandable balloon, wherein the support is made of surgical stainless steel and is expandable using the balloon.

27. The support of claim 25, wherein the support is made of a memory metal and is configured to self-expand toward the expanded diameter.

28. A support for a vascular prosthesis, comprising:
  at least one row of interconnected foreshortening cells extending circumferentially around a longitudinal axis of the support, each of the foreshortening cells having a circumferential axis in the circumferential direction and a long axis in the longitudinal direction, the support having a proximal end and a distal end and being expandable from a compacted diameter to an expanded diameter, the foreshortening cells being configured so that when the support is expanded from the compacted diameter to the expanded diameter, the circumferential axis of each foreshortening cell increases while simultaneously the long axis of each foreshortening cell decreases;
  an elongate distal prong extending from a foreshortening cell in one of the at least one row of interconnected foreshortening cells, the elongate distal prong extending generally radially outwardly from the foreshortening cell and generally axially toward the proximal end of the support; and
  an elongate proximal prong extending from the support proximal of the distal prong, the elongate proximal prong extending generally radially outwardly relative to the foreshortening cells of the support and generally axially toward the distal end of the support so that a space is defined between tips of the proximal and distal prongs and the distal prong tip is distal of the proximal prong tip;
  wherein the prongs are bent when the support is radially expanded so that a first portion of each prong, which first portion is spaced from the prong tip, extends outwardly relative to the longitudinal axis of the support, and the prongs are further bent so that a second portion of the prong adjacent the prong tip extends inwardly relative to the outwardly-bent first portion; and
  wherein when the support is radially expanded a longitudinal distance between the tips of the proximal and distal prongs decreases.

29. The support of claim 28, wherein the prongs are configured so that when the support is expanded from the compacted diameter to the expanded diameter so that the longitudinal distance between the tips of the proximal and distal prongs decreases, body tissue in the space between the tips of the proximal and distal prongs is engaged by the prongs sufficient to form a stable connection between the support and the tissue.

30. The support of claim 29, wherein the prongs exert a generally longitudinally-directed force on the tissue engaged therebetween.

31. The support of claim 30 additionally comprising a percutaneous replacement heart valve attached inside the support, and the support is sized and configured so that the prongs axially engage tissue as the support is radially expanded so as to anchor the support within a native heart valve opening.

32. The support of claims 31, wherein in the expanded configuration the distal and proximal prongs each comprise a substantially straight portion, and the straight portions are generally parallel to the longitudinal axis of the support.

33. The support of claim 32, wherein the support is made of a memory metal material, and is configured to self-expand from the compacted diameter toward the expanded diameter, and wherein a memory shape of the prongs is to comprise a base portion that bends radially outwardly relative to the corresponding foreshortening cell, and an elongate portion that extends generally straight and parallel to the longitudinal axis of the support.

34. The support of claim 33, wherein the proximal and distal prongs extend longitudinally toward one another when the support is in the compacted diameter.

35. The support of claim 28, wherein the elongate proximal prong extends from a foreshortening cell in one of the at least one row of interconnected foreshortening cells.

36. A support for a vascular prosthesis, comprising:
  a support body comprising an array of interconnected cells extending circumferentially around a longitudinal axis of the support, the support body having a proximal end and a distal end and being radially expandable from a compacted state to an expanded state;
  an elongate distal prong extending from the support body, the elongate distal prong extending generally toward the proximal end of the support body so that a tip of the distal prong is longitudinally proximal of a base of the distal prong;
  an elongate proximal prong extending from the support body, the elongate proximal prong extending generally toward the distal end of the support body so that a tip of the proximal prong is longitudinally distal of a base of the proximal prong and the tip of the proximal prong is proximal of the tip of the distal prong;
  the prongs bent when in the expanded state so that a first portion of each prong adjacent the prongs base is bent outwardly relative to the longitudinal axis of the support and the prongs are further bent so that a second portion of the prong adjacent the prong tip is directed inwardly relative to the outwardly-bent first portion;
  the support body comprising a foreshortening portion between at least the tips of the distal and proximal prongs, the foreshortening portion configured to longitudinally shorten as the support body is radially expanded from the compacted state to the expanded state;
  wherein when the support body is radially expanded from the compacted state to the expanded state a longitudinal distance between the tips of the proximal and distal prongs decreases; and
  wherein when the support body is in the expanded state the distal prong extends generally radially outwardly from the support body and toward the proximal end of the support body, and the proximal prong extends generally radially outwardly from the support body and toward the distal end of the support body.

37. The support of claim 36, wherein the interconnected cells in the foreshortening portion are each defined by a plurality of interconnected struts, and wherein when the support body is radially expanded a shape of each cell in the foreshortening portion changes.

38. The support of claim 37, wherein when the support body is in the compacted state the cells in the foreshortening portion are generally oval-shaped, and when the support body is in the expanded state the cells in the foreshortening portion are generally diamond-shaped.

39. The support of claim 36, wherein the prongs are configured so that when the support body is radially expanded from the compacted state to the expanded state so that the longitudinal distance between the tips of the proximal and distal prongs decreases, body tissue in a space between the tips of the proximal and distal prongs is engaged by the prongs sufficient to form a stable connection between the support and the tissue.

40. The support of claim 39, wherein the prongs exert a generally longitudinally-directed force on the tissue engaged therebetween.

41. The support of claim 40 additionally comprising a percutaneous replacement heart valve attached inside the support body, and the support is sized and configured so that the prongs axially engage tissue as the support is radially expanded so as to anchor the support within a native heart valve opening.

42. The support of claims 41, wherein in the expanded state the second portions of the prongs are substantially straight and generally parallel to the longitudinal axis of the support.

43. The support of claim 42, wherein in the expanded state the first portions of the prongs are substantially straight, and a second bend point is defined between the first and second portions.

44. The support of claim 36, wherein the elongate distal prong extends from one of the cells in the foreshortening portion.

45. The support of claim 44, wherein the elongate proximal prong extends from one of the cells in the foreshortening portion.

* * * * *